US00PP20883P2

(12) United States Plant Patent
Whiting

(10) Patent No.: US PP20,883 P2
(45) Date of Patent: Mar. 23, 2010

(54) ***CHAMAECYPARIS* PLANT NAMED 'DOW WHITING'**

(50) Latin Name: *Chamaecyparis pisifera*
Varietal Denomination: Dow Whiting

(75) Inventor: Dow Whiting, Nixa, MO (US)

(73) Assignee: Spring Meadow Nursery, Inc., Grand Haven, MI (US)

( * ) Notice: Subject to any disclaimer, the term of this patent is extended or adjusted under 35 U.S.C. 154(b) by 0 days.

(21) Appl. No.: 12/313,677

(22) Filed: Nov. 21, 2008

(51) Int. Cl.
*A01H 7/00* (2006.01)

(52) U.S. Cl. ..... Plt./213

(58) Field of Classification Search ..... Plt./213
See application file for complete search history.

(56) References Cited

OTHER PUBLICATIONS

Upov-rom Plant Variety Database 2009/03, GTI Jouve Retrieval Software. Citation for *Chamaecyparis* 'Dow Whiting' one page.*

* cited by examiner

*Primary Examiner*—June Hwu
(74) *Attorney, Agent, or Firm*—C. A. Whealy

(57) ABSTRACT

A new and distinct cultivar of *Chamaecyparis* plant named 'Dow Whiting', characterized by its compact and pyramidal plant form; leaves with rich green-colored upper surfaces and silvery blue-colored lower surfaces; and winter hardiness.

1 Drawing Sheet

Botanical designation: *Chamaecyparis pisifera.*
Cultivar denomination: 'Dow Whiting'.

BACKGROUND OF THE INVENTION

The present Invention relates to a new and distinct cultivar of *Chamaecyparis* plant, botanically known as *Chamaecyparis pisifera*, and hereinafter referred to by the name 'Dow Whiting'.

The new *Chamaecyparis* plant is a naturally-occurring branch mutation of *Chamaecyparis pisifera* 'Boulevard', not patented. The new *Chamaecyparis* plant was discovered and selected by the Inventor on a single plant of 'Boulevard' within a population of plants of 'Boulevard' in a controlled outdoor nursery environment in Highlandville, Mo. in May, 2000.

Asexual reproduction of the new *Chamaecyparis* plant by hardwood cuttings in a controlled greenhouse environment in Highlandville, Mo. since November, 2000, has shown that the unique features of this new *Chamaecyparis* plant are stable and reproduced true to type in successive generations.

SUMMARY OF THE INVENTION

Plants of the new *Chamaecyparis* have not been observed under all possible environmental conditions. The phenotype may vary somewhat with variations in environment and culture such as temperature and light intensity without, however, any variance in genotype.

The following traits have been repeatedly observed and are determined to be the unique characteristics of the new *Chamaecyparis* plant. These characteristics in combination distinguish 'Dow Whiting' as a new and distinct cultivar of *Chamaecyparis:*

1. Compact and pyramidal plant form.
2. Leaves with rich green-colored upper surfaces and silvery blue-colored lower surfaces.
3. Winter hardy.

Plants of the new *Chamaecyparis* are most similar to plants of the parent, 'Boulevard'. Plants of the new *Chamaecyparis* differ from plants of 'Boulevard' in the following characteristics:

1. Plants of the new *Chamaecyparis* are broader than and not as narrow as 'Boulevard'.
2. Upper surfaces of leaves of plants of the new *Chamaecyparis* are rich green in color whereas upper surfaces of leaves of plants of 'Boulevard' are silvery blue in color.

Plants of the new *Chamaecyparis* can also be compared to plants of *Chamaecyparis pisifera* 'Mr. Green Genes', not patented. Plants of the new *Chamaecyparis* differ from plants of 'Mr. Green Genes' in the following characteristics:

1. Plants of the new *Chamaecyparis* are more compact than and not as vigorous as plants of 'Mr. Green Genes'.
2. Plants of the new *Chamaecyparis* are more uniform in shape than plants of 'Mr. Green Genes'.
3. Plants of the new *Chamaecyparis* and 'Mr. Green Genes' differ in leaf color as plants of 'Mr. Green Genes' have lighter green-colored leaves.
4. Leaves of plants of the new *Chamaecyparis* are green in color throughout the year whereas leaves of plants of 'Mr. Green Genes' tend to turn brown during the winter.

Plants of the new *Chamaecyparis* can also be compared to plants of *Chamaecyparis pisifera* 'Cream Ball', not patented. Plants of the new *Chamaecyparis* differ from plants of 'Cream Ball' in the following characteristics:

1. Plants of the new *Chamaecyparis* are more compact than plants of 'Cream Ball'.
2. Plants of the new *Chamaecyparis* are more uniform in shape than plants of 'Cream Ball'.
3. Plants of the new *Chamaecyparis* and 'Cream Ball' differ in lower surface leaf color as plants of 'Cream Ball' have creamy white-colored lower leaf surfaces.

BRIEF DESCRIPTION OF THE PHOTOGRAPHS

The accompanying colored photographs illustrate the overall appearance of the new *Chamaecyparis* plant, showing the colors as true as it is reasonably possible to obtain in colored reproductions of this type. Colors in the photographs may differ slightly from the color values cited in the detailed botanical description which accurately describe the colors of the new *Chamaecyparis* plant.

The photograph at the bottom of the sheet is a side perspective view of a typical plant of 'Dow Whiting' grown in an outdoor nursery.

The photograph at the top of the sheet is a close-up view of the foliage of a typical plant of 'Dow Whiting'.

DETAILED BOTANICAL DESCRIPTION

Plants used for the aforementioned photographs and following observations and measurements were grown in Grand Haven, Mich. during the summer in an outdoor nursery and under conditions which approximate commercial *Chamaecyparis* production. Plants had been growing for three years when the photographs and description were taken. In the following description, color references are made to The Royal Horticultural Society Colour Chart, 1995 Edition, except where general terms of ordinary dictionary significance are used.

Botanical classification: *Chamaecyparis pisifera* 'Dow Whiting'.

Parentage: Naturally-occurring branch mutation of *Chamaecyparis pisifera* 'Boulevard', not patented.

Propagation:

*Type*.—By hardwood cuttings.

*Time to initiate roots*.—About 40 days at 20° C.

*Time to produce a rooted young plant*.—About 120 days at 20° C.

*Root description*.—Thick.

*Rooting habit*.—Freely branching; dense.

Plant description:

*Form/growth habit*.—Compact evergreen shrub, pyramidal plant form; moderately vigorous growth habit.

*Branching habit*.—Freely branching with numerous lateral branches developing per plant. Branches mostly horizontal to slightly arching. Plants maintain their lower branches and foliage at the soil level.

*Plant height*.—About 1.25 meters.

*Plant diameter*.—About 60 cm.

*Trunk texture*.—Rough.

*Lateral branch description*.—Length: About 18 cm. Diameter: About 3.5 mm. Texture: Smooth, scaly. Strength: Strong. Color, developing: Close to 145A. Color, mature: Close to 177B.

*Leaf description*.—Appearance/arrangement: Scale-like, flat; opposite; sessile. Length: About 1 mm. Width: About 0.75 mm. Shape: Scale-like. Apex: Acute. Base: Cuneate. Margin: Entire. Texture, upper and lower surface: Smooth, glabrous. Venation pattern: Parallel. Color: Developing leaves, upper and lower surfaces: Close to 144A. Fully expanded leaves, upper surface: Close to 141A; venation, close to 141A. Fully expanded leaves, lower surface: Close to 141B overlain with close to 190D giving a silvery blue color; venation, close to 141 B overlain with close to 190D.

*Cone description*.—Cone development has not been observed.

Disease/pest resistance: Plants of the new *Chamaecyparis* have not been noted to be resistant to pathogens or pests common to *Chamaecyparis*.

Weather tolerance: Plants of the new *Chamaecyparis* have been observed to be tolerant to drought, rain, wind and temperatures ranging from about −20° C. to about 30° C.

It is claimed:

1. A new and distinct *Chamaecyparis* plant named 'Dow Whiting' as illustrated and described.

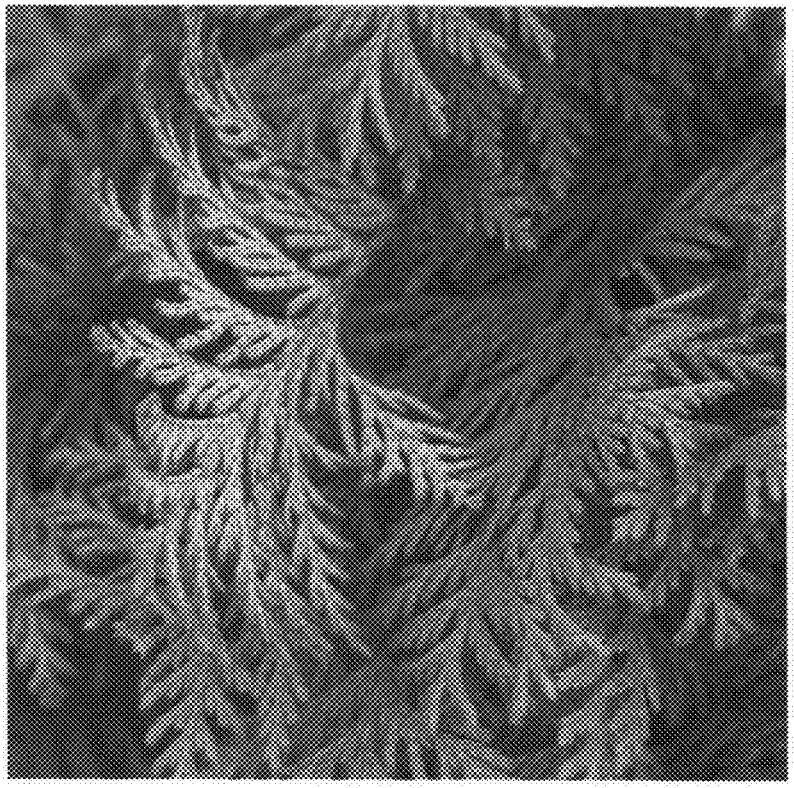
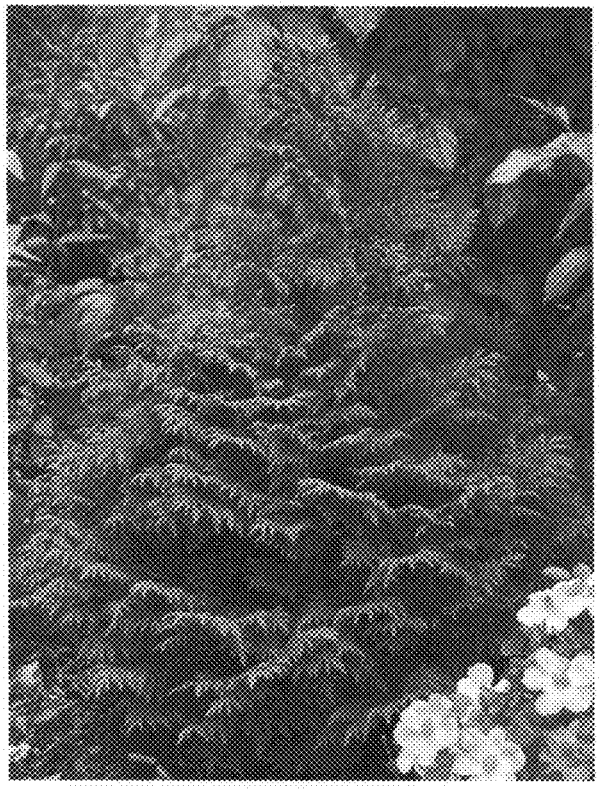

* * * * *